United States Patent [19]

Doria et al.

[11] Patent Number: 4,826,837
[45] Date of Patent: May 2, 1989

[54] CINNOLINE-CARBOXAMIDES AND PROCESS FOR THEIR PREPARATION

[75] Inventors: Gianfederico Doria; Anna M. Isetta; Mario Ferrari; Domenico Trizio, all of Milan, Italy

[73] Assignee: Farmitalia Carlo Erba s.r.l., Milan, Italy

[21] Appl. No.: 148,702

[22] Filed: Jan. 26, 1988

[30] Foreign Application Priority Data

Feb. 2, 1987 [GB] United Kingdom ................. 8702288

[51] Int. Cl.$^4$ ............................................. A61K 31/50
[52] U.S. Cl. .................................. 514/248; 514/212; 514/228.2; 514/524.5
[58] Field of Search ................ 540/599; 544/235, 116, 544/62; 514/212, 248, 228.2, 234.5

[56] References Cited

U.S. PATENT DOCUMENTS

| | | | |
|---|---|---|---|
| 4,027,023 | 5/1977 | Preston et al. | 544/235 |
| 4,045,439 | 8/1977 | Preston et al. | 544/235 |
| 4,085,103 | 4/1978 | Preston et al. | 544/235 |

FOREIGN PATENT DOCUMENTS 205272 12/1986 European Pat. Off. ............ 544/235

Primary Examiner—Mary C. Lee
Assistant Examiner—R. B. Magrab
Attorney, Agent, or Firm—Armstrong, Nikaido Marmelstein & Kubovcik

[57] ABSTRACT

The invention relates to compounds having the general formula (I)

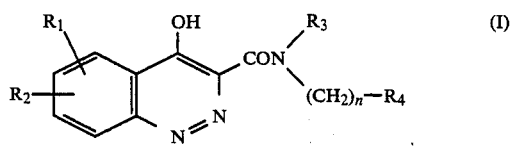

wherein n is zero, 1 or 2;
each of $R_1$ and $R_2$ is independently:
 (a) hydrogen, halogen, trifluoromethyl or $C_1$-$C_6$ alkyl;
 (b) hydroxy, $C_1$-$C_6$ alkoxy or $C_3$-$C_4$ alkenyloxy;
 (c) nitro, amino, formylamino or $C_2$-$C_8$ alkanoylamino;
$R_3$ represents hydrogen or $C_1$-$C_8$ alkyl;
$R_4$ is:
 (a') $C_1$-$C_{20}$ alkyl, unsubstituted or substituted by

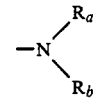

wherein each of $R_a$ and $R_b$ is independently phenyl or $C_1$-$C_6$ alkyl, or $R_a$ and $R_b$, taken together with the nitrogen atom to which they are linked, form a N-pyrrolidinyl, N-piperazinyl, hexahydroazepin-1-yl, thiomorpholino, morpholino or piperidino ring, wherein said heterocyclic rings may be unsubstituted or substituted by $C_1$-$C_6$ alkyl or phenyl;
 (b') $C_5$-$C_{10}$ cycloalkyl, unsubstituted or substituted by methyl;
 (c') 2- or 3-pyrrolidinyl, piperidyl of 2-piperazinyl, wherein said heterocyclic rings may be unsubstituted or substituted by $C_1$-$C_6$ alkyl;
 (d') isoxazolyl or thiazolyl, wherein said heterocyclic rings may be unsubstituted or substituted by $C_1$-$C_6$ alkyl;
 (e') pyridyl, unsubstituted or substituted by one or two substituents chosen independently from halogen, $C_1$-$C_6$ alkyl and $C_1$-$C_6$ alkoxy; or
 (f') phenyl, unsubstituted or substituted by one or two substituents chosen independently from halogen, $CF_3$, $C_1$-$C_6$ alkyl, $C_1$-$C_6$ alkoxy, amino, nitro, formylamino and $C_2$-$C_8$ alkanoylamino, and the pharmaceutically acceptable salts thereof, which possess immunomodulating activity and are useful e.g. in the treatment of neoplastic diseases and acute and chronic infections of both bacterial and viral origin in mammals.

8 Claims, No Drawings

CINNOLINE-CARBOXAMIDES AND PROCESS FOR THEIR PREPARATION

The present invention relates to 4-hydroxycinnoline-carboxamides, to their use as immunomodulating agents, to a method for their preparation and pharmaceutical compositions containing them.

The preparation of cinnoline compounds, including 4-hydroxycinnoline-3-carboxylic acids, is described in "A new Cinnoline synthesis. Part I. Cyclization of Mesoxalyl Chloride to give substituted 4-hydroxycinnoline-3-carboxylic acids". J. Chem. Soc. 2828 (1961).

The synthesis of 4-hydroxycinnoline-3-carboxylic alkyl esters, useful as intermediate compounds for the preparation of pirazolo-cinnolines having anxiolytic properties, is also described in French Pat. No. 2 549 833.

Additionally 4-hydroxy-3-cinnoline carboxamides are described in U.S. Pat. No. 3,657,241. However no utility is attributed to such compounds, which are intermediate compounds in the preparation of the corresponding 4-halocinnolines useful as herbicides, fungicides and insecticides.

The broad general formula of the compounds object of European patent application publication No. 205272 embraces 4-amino- and 4-hydroxy-cinnoline-3-carboxylic acid derivatives, to which CNS depressant activity is attributed. However, besides the sole compounds: 4-hydroxy-N,8-dipropyl-cinnoline-3-carboxamide and 8-chloro-4-hydroxy-N-propyl-cinnoline-3-carboxamide, no further 4-hydroxycinnoline-3-carboxamide derivative is specifically mentioned in the European document.

Moreover none of the foregoing prior-art documents discloses or suggests the use of the compounds of the present invention as immunomodulating agents or their use in the preparation of a pharmaceutical composition having immunomodulating activity.

It has now been found that 4-hydroxy-3-cinnoline carboxamides of general formula (I), as herein defined, and the pharmaceutically acceptable salts thereof possess immunomodulating activity.

The present invention therefore relates, as a first object, to the use of a compound of formula (I), or a pharmaceutically acceptable salt thereof, as immunomodulator, to pharmaceutical compositions having immunomodulating activity containing a compound of formula (I), or a pharmaceutically acceptable salt thereof, as active principle and to the use of a compound of formula (I), or a pharmaceutically acceptable salt thereof, for the preparation of these pharmaceutical compositions. The compounds of formula (I) have the following general formula

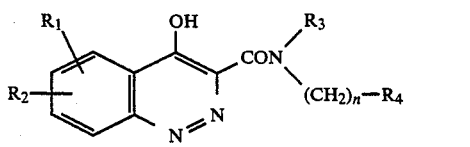

wherein
n is zero, 1 or 2;
each of $R_1$ and $R_2$ is independently:
  (a) hydrogen, halogen, trifluoromethyl or $C_1$–$C_6$ alkyl;
  (b) hydroxy, $C_1$–$C_6$ alkoxy or $C_3$–$C_4$ alkenyloxy;
  (c) nitro, amino, formylamino or $C_2$–$C_8$ alkanoylamino;
$R_3$ represents hydrogen or $C_1$–$C_8$ alkyl;
$R_4$ is:
  (a') $C_1$–$C_{20}$ alkyl, unsubstituted or substituted by

wherein each of $R_a$ and $R_b$ is independently phenyl or $C_1$–$C_6$ alkyl, or $R_a$ and $R_b$, taken together with the nitrogen atom to which they are linked, form a N-pyrrolidinyl, N-piperazinyl, hexahydroazepin-1-yl, thiomorpholino, morpholino or piperidino ring, wherein said heterocyclic rings may be unsubstituted or substituted by $C_1$–$C_6$ alkyl or phenyl;
  (b') $C_5$–$C_{10}$ cycloalkyl, unsubstituted or substituted by methyl;
  (c') 2- or 3-pyrrolidinyl, piperidyl of 2-piperazinyl, wherein said heterocyclic rings may be unsubstituted or substituted by $C_1$–$C_6$ alkyl;
  (d') isoxazolyl or thiazolyl, wherein said heterocyclic rings may be unsubstituted or substituted by $C_1$–$C_6$ alkyl;
  (e') pyridyl, unsubstituted or substituted by one or two substituents chosen independently from halogen, $C_1$–$C_6$ alkyl and $C_1$–$C_6$ alkoxy; or
  (f') phenyl, unsubstituted or substituted by one or two substituents chosen independently from halogen, $CF_3$, $C_1$–$C_6$ alkyl, $C_1$–$C_6$ alkoxy, amino, nitro, formylamino and $C_2$–$C_8$ alkanoylamino.

These compounds and their salts are hereafter referred to as the "active compounds" and as the "compounds of the invention".

By evaluating the prior-art references cited above, it appears clear that two of the compounds, failing within the general formula (I) above, are known compounds previously mentioned in Ep-A-205272; others are embraced by the broad general formula of the European document, but therein not specifically mentioned; whereas other compounds of general formula (I) are not covered by the foregoing prior-art documents.

It has to be noticed that the 4-hydroxy-cinnoline derivatives of general formula (I) may exist also in the tautomer cinnolone form of general formula

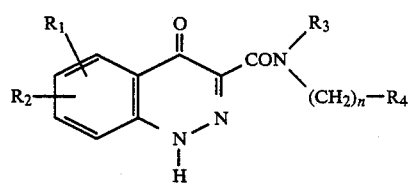

Nevertheless all the compounds of the present invention are named as 4-hydroxy-cinnoline derivatives.

The invention also includes within its scope all the possible isomers, stereoisomers and optical isomers and their mixtures, and the metabolites and the metabolic precursors or bioprecursors of the compounds of formula (I).

A halogen atom is preferably chlorine or fluorine. The alkyl, alkenyloxy, alkoxy and alkanoylamino groups may be branched or straight chain groups.

A $C_1$–$C_{20}$ alkyl group is preferably a $C_1$–$C_{16}$ in particular $C_1$–$C_8$ alkyl group.

A $C_1$–$C_8$ alkyl group is preferably a $C_1$–$C_6$ alkyl group.

A $C_1$–$C_6$ alkyl is, e.g., methyl, ethyl, propyl, isopropyl, butyl or tert.butyl, more preferably, methyl, ethyl or tert. butyl.

A $C_3$–$C_4$ alkenyloxy group is preferably allyloxy.

A $C_1$–$C_6$ alkoxy group is, e.g., methoxy, ethoxy, propoxy, isopropoxy, butoxy or tert.butoxy, preferably it is methoxy, ethoxy or propoxy.

A $C_5$–$C_{10}$ cycloalkyl group is preferably cyclopentyl, cyclohexyl or cycloheptyl.

A $C_2$–$C_8$ alkanoylamino group is preferably acetylamino or propionylamino.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic and sulphuric acids and with organic acids, e.g. citric tartaric, maleic, malic, fumaric, methanesulphonic and ethanesulphonic acids.

Preferred salts of the compounds of formula (I) are the sodium and the potassium salts thereof.

As stated above, the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are those of formula (I) wherein:

n is zero, 1 or 2;

each of $R_1$ and $R_2$ is independently hydrogen, halogen, trifluoromethyl, $C_1$–$C_4$ alkyl, nitro, amino or $C_1$–$C_4$ alkoxy;

$R_3$ represents hydrogen or $C_1$–$C_4$ alkyl;

$R_4$ is:

(a″) $C_1$–$C_{16}$ alkyl, unsubstituted or substituted by

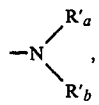

wherein $R'_a$ and $R'_b$ are independently $C_1$–$C_4$ alkyl or $R'_a R'_b$, taken together with the nitrogen atom to which are linked, form a N-pirrolidinyl, N-piperazinyl, morpholino or piperidino ring, wherein said heterocyclic rings may be unsubstituted or substituted by $C_1$–$C_2$ alkyl;

(b″) $C_5$–$C_7$ cycloalkyl, unsubstituted or substituted by methyl;

(c″) 2- or 3-pyrrolidinyl, piperidyl, isoxazolyl or thiazolyl, wherein said heterocyclic rings may be unsubstituted or substituted by $C_1$–$C_2$ alkyl;

(d″) pyridyl, unsubstituted or substituted by one or two substituents chosen independently from halogen, $C_1$–$C_2$ alkyl and $C_1$–$C_2$ alkoxy; or (e″) phenyl, unsubstituted or substituted by one or two substituents chosen independently from halogen, $CF_3$, $C_1$–$C_4$ alkyl, $C_1$–$C_4$ alkoxy, nitro and amino; and the pharmaceutically acceptable salts thereof.

More preferred compounds of the invention are those of formula (I) wherein:

n is zero, 1 or 2;

each of $R_1$ and $R_2$ is independently hydrogen, halogen, trifluoromethyl, $C_1$–$C_4$ alkyl or $C_1$–$C_4$ alkoxy;

$R_3$ represents hydrogen or $C_1$–$C_2$ alkyl;

$R_4$ is:

(a‴) $C_1$–$C_8$ alkyl, unsubstituted or substituted by di ($C_1$–$C_2$) alkylamino, morpholino, or piperidino, or by a N-pyrrolidinyl or N-($C_1$–$C_2$)alkyl-N-piperazinyl ring;

(b‴) $C_5$–$C_6$ cycloalkyl, unsubstituted or substituted by methyl;

(c‴) 2- or 3-pyrrolidinyl or isoxazolyl, wherein said heterocyclic rings may be unsubstituted or substituted by $C_1$–$C_2$ alkyl;

(d‴) pyridyl, unsubstituted or substituted by chlorine, bromine, methyl or methoxy; or (e‴) phenyl, unsubstituted or substituted by halogen, $CF_3$, $C_1$–$C_4$ alkyl, $C_1$–$C_4$ alkoxy, nitro or amino; and the the pharmaceutically acceptable salts thereof, Examples of particularly preferred compounds of the invention are:

4-hydroxy-N-(4-pyridyl)-cinnoline-3-carboxamide;
4-hydroxy-N-(2-pyridyl)-cinnoline-3-carboxamide;
4-hydroxy-N-(3-pyridyl)-cinnoline-3-carboxamide;
4-hydroxy-N-(6-methyl-2-pyridyl)-cinnoline-3-carboxamide;
4-hydroxy-N-phenyl-cinnoline-3-carboxamide;
4-hydroxy-N-methyl-N-(2-pyridyl)-cinnoline-3-carboxamide;
4-hydroxy-N-(3-methyl-2-pyridyl)-cinnoline-3-carboxamide;
4-hydroxy-N-(4-methyl-2-pyridyl)-cinnoline-3-carboxamide;
N-cyclohexyl-4-hydroxy-cinnoline-3-carboxamide;
N-(3-chloro-phenyl)-4-hydroxy-cinnoline-3-carboxamide;
N-benzyl-4-hydroxy-cinnoline-3-carboxamide;
4-hydroxy-6-methoxy-N-(2-pyridyl)-cinnoline-3-carboxamide;
4-hydroxy-N-phenethyl-cinnoline-3-carboxamide;
4-hydroxy-N-(3-methyl-phenyl)-cinnoline-3-carboxamide;
4-hydroxy-N-(3-methoxy-phenyl)-cinnoline-3-carboxamide;
N-(4-fluoro-benzyl)-4-hydroxy-cinnoline-3-carboxamide;
N-butyl-4-hydroxy-cinnoline-3-carboxamide;
4-hydroxy-N-(2-methyl-phenyl)-cinnoline-3-carboxamide;
4-hydroxy-N-(2-methoxy-phenyl)-cinnoline-3-carboxamide;
N-(2-chloro-phenyl)-4-hydroxy-cinnoline-3-carboxamide;
4-hydroxy-N-(3-nitro-phenyl)-cinnoline-3-carboxamide;
N-(3-amino-phenyl)-4-hydroxy-cinnoline-3-carboxamide;
4-hydroxy-N-(3-trifluoromethyl-phenyl)-cinnoline-3-carboxamide;

N-(3-bromo-phenyl)-4-hydroxy-cinnoline-3-carboxamide;
N-(3,5-dichloro-phenyl)-4-hydroxy-cinnoline-3-carboxamide;
N-(2,3-dichloro-phenyl)-4-hydroxy-cinnoline-3-carboxamide;
N-(4-fluoro-phenyl)-4-hydroxy-cinnoline-3-carboxamide;
N-(3-fluoro-phenyl)-4-hydroxy-cinnoline-3-carboxamide;
4-hydroxy-6-methyl-N-(2-pyridyl)-cinnoline-3-carboxamide;
6-chloro-4-hydroxy-N-(2-pyridyl)-cinnoline-3-carboxamide;
6-chloro-N-(4-fluoro-phenyl)-4-hydroxy-cinnoline-3-carboxamide;
6-chloro-N-(3-fluoro-phenyl)-4-hydroxy-cinnoline-3-carboxamide;
6-chloro-N-(3-chloro-phenyl)-4-hydroxy-cinnoline-3-carboxamide;
6-chloro-4-hydroxy-N-(3-methyl-phenyl)-cinnoline-3-carboxamide;
6-chloro-4-hydroxy-N-(6-methyl-2-pyridyl)-cinnoline-3-carboxamide;
6-chloro-4-hydroxy-N-phenyl-cinnoline-3-carboxamide;
4-hydroxy-6-methyl-N-phenyl-cinnoline-3-carboxamide;
4-hydroxy-6-methoxy-N-phenyl-cinnoline-3-carboxamide;
N-benzyl-6-chloro-4-hydroxy-cinnoline-3-carboxamide;
N-benzyl-4-hydroxy-6-methyl-cinnoline-3-carboxamide;
N-benzyl-4-hydroxy-6-methoxy-cinnoline-3-carboxamide;
4-hydroxy-N-(2,6-dimethyl-phenyl)-cinnoline-3-carboxamide;
6-fluoro-4-hydroxy-N-phenyl-cinnoline-3-carboxamide;
6-fluoro-4-hydroxy-N-(2-pyridyl)-cinnoline-3-carboxamide;
N-benzyl-6-fluoro-4-hydroxy-cinnoline-3-carboxamide;
6-fluoro-N-(4-fluoro-phenyl9-4-hydroxy-cinnoline-3-carboxamide;
6-fluoro-N-(3-fluoro-phenyl)-4-hydroxy-cinnoline-3-carboxamide;
6-fluoro-4-hydroxy-N-(6-methyl-2-pyridyl)-cinnoline-3-carboxamide;
N-(3-chloro-phenyl)-6-fluoro-4-hydroxy-cinnoline-3-carboxamide;
4-hydroxy-N-(3-dimethylamino-propyl)-cinnoline-3-carboxamide;
4-hydroxy-N-(2-dimethylamino-ethyl)-cinnoline-3-carboxamide;
4-hydroxy-N-(2-morpholino-ethyl)-cinnoline-3-carboxamide;
4-hydroxy-N-[2-(1-methyl-pyrrolidin-2-yl)-ethyl]-cinnoline-3-carboxamide;
N-[(1-ethyl-pyrrolidin-2-yl)-methyl]-4-hydroxy-cinnoline-3-carboxamide;
and the pharmaceutically acceptable salts thereof, in particular the sodium and the potassium salts.

A selected class of active compounds of formula (I) are those of formula (Ia)

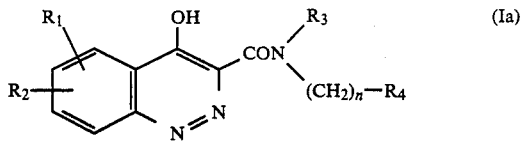

wherein
n is zero, 1 or 2;
each of $R_1$ and $R_2$ is independently:
(a) hydrogen, halogen, trifluoromethyl or $C_1$–$C_6$ alkyl;
(b) hydroxy, $C_1$–$C_6$ alkoxy or $C_3$–$C_4$ alkenyloxy;
(c) nitro, amino, formylamino or $C_2$–$C_8$ alkanoylamino;
$R_3$ represents hydrogen or $C_1$–$C_8$ alkyl;
$R_4$ is:
(a') $C_1$–$C_{20}$ alkyl, unsubstituted or substituted by

wherein each of $R_a$ and $R_b$ is independently phenyl or $C_1$–$C_6$ alkyl, or $R_a$ and $R_b$, taken together with the nitrogen atom to which they are linked, form a N-pyrrolidinyl, N-piperazinyl, hexahydroazepin-1-yl, thiomorpholino, morpholino or piperidino ring, wherein said heterocyclic rings may be unsubstituted or substituted by $C_1$–$C_6$ alkyl or phenyl;
(b') $C_5$–$C_{10}$ cycloalkyl, unsubstituted or substituted by methyl;
(c') 2- or 3-pyrrolidinyl, piperidyl or 2-piperazinyl, wherein said heterocyclic rings may be unsubstituted or substituted by $C_1$–$C_6$ alkyl;
(d') isoxazolyl or thiazolyl, wherein said heterocyclic rings may be unsubstituted or substituted by $C_1$–$C_6$ alkyl;
(e') pyridyl, unsubstituted or substituted by one or two substituents chosen independently from halogen, $C_1$–$C_6$ alkyl and $C_1$–$C_6$ alkoxy; or
(f') phenyl, unsubstituted or substituted by one or two substituents chosen independently from halogen, $CF_3$, $C_1$–$C_6$ alkyl, $C_1$–$C_6$ alkoxy, amino, nitro, formylamino and $C_2$–$C_8$ alkanoylamino; and the pharmaceutically acceptable salts thereof, and wherein, when $R_4$ is unsubstituted $C_1$–$C_{10}$ alkyl or unsubstituted $C_5$–$C_6$ cycloalkyl, then at least one of $R_1$ and $R_2$ is formylamino or $C_2$–$C_8$ alkanoylamino.

None of the compounds of formula (Ia) falling within the general formula disclosed in EP-A-205272 is therein specifically mentioned. The compounds of general formula (Ia), and their pharmaceutically acceptable salts, therefore are the second object of the present invention. A further object of the present invention is to provide a pharmaceutical composition containing as active principle a compound of formula (Ia) or a pharmaceutically acceptable salt thereof. Preferred compounds of formula (Ia), as defined above, are those wherein:
n is zero, 1 or 2;
each of $R_1$ and $R_2$ is independently hydrogen, halogen, trifluoromethyl, $C_1$–$C_4$ alkyl, nitro, amino or $C_1$–$C_4$ alkoxy;
$R_3$ represents hydrogen or $C_1$–$C_4$ alkyl;
$R_4$ is:

($a_1$) unsubstituted $C_{11}$–$C_{16}$ alkyl;
($b_1$) $C_1$–$C_{16}$ alkyl substituted by

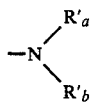

wherein $R'_a$ and $R'_b$ are independently $C_1$–$C_4$ alkyl or $R'_a$ and $R'_b$ taken together with the nitrogen atom to which they are linked, form a N-pyrrolidinyl, N-piperazinyl, morpholino or piperidino ring, wherein said heterocyclic rings may be unsubstituted or substituted by $C_1$–$C_2$ alkyl;

($c_1$) cyclohexyl substituted by methyl;
($d_1$) 2- or 3-pyrrolidinyl, piperidyl, isoxazolyl or thiazolyl, wherein said heterocyclic rings may be unsubstituted or substituted by $C_1$–$C_2$ alkyl;
($e_1$) pyridyl, unsubstituted or substituted by one or two substituents chosen independently from halogen, $C_1$–$C_2$ alkyl and $C_1$–$C_2$ alkoxy; or
($f_1$) phenyl, unsubstituted or substituted by one or two substituents chosen independently from halogen, $CF_3$, $C_1$–$C_4$ alkyl, $C_1$–$C_4$ alkoxy, nitro and amino; and the pharmaceutically acceptable salts thereof.

Most preferred compounds of formula (1a), as defined above, are those wherein
n is zero, 1 or 2;
each of $R_1$ and $R_2$ is independently hydrogen, halogen, trifluoromethyl, $C_1$–$C_4$ alkyl or $C_1$–$C_4$ alkoxy;
$R_3$ represents hydrogen or $C_1$–$C_2$ alkyl;
$R_4$ is:
($a_2$) $C_1$–$C_8$ alkyl substituted by di($C_1$–$C_2$)alkyl-amino, morpholino or piperidino, or by a N-pyrrolidinyl or N-($C_1$–$C_2$) alkyl-N-piperazinyl ring;
($b_2$) 2- or 3-pyrrolidinyl or isoxazolyl, wherein said heterocyclic rings may be unsubstituted or substituted by $C_1$–$C_2$ alkyl;
($c_2$) pyridyl, unsubstituted or substituted by chlorine, bromine, methyl or methoxy; or
($d_2$) phenyl, unsubstituted or substituted by halogen, $CF_3$, $C_1$–$C_4$ alkyl, $C_1$–$C_4$ alkoxy, nitro or amino; and the pharmaceutically acceptable salts thereof.

As specific examples of compounds having general formula (Ia), the following can be mentioned:
4-hydroxy-N-(4-pyridyl)-cinnoline-3-carboxamide;
4-hydroxy-N-(2-pyridyl)-cinnoline-3-carboxamide;
4-hydroxy-N-(3-pyridyl)-cinnoline-3-carboxamide;
4-hydroxy-N-(6-methyl-2-pyridyl)-cinnoline-3-carboxamide;
4-hydroxy-N-phenyl-cinnoline-3-carboxamide;
4-hydroxy-N-methyl-N-(2-pyridyl)-cinnoline-3-carboxamide;
4-hydroxy-N-(3-methyl-2-pyridyl)-cinnoline-3-carboxamide;
4-hydroxy-N-(4-methyl-2-pyridyl)-cinnoline-3-carboxamide;
N-(3-chloro-phenyl)-4-hydroxy-cinnoline-3-carboxamide;
N-benzyl-4-hydroxy-cinnoline-3-carboxamide;
4-hydroxy-6-methoxy-N-(2-pyridyl)-cinnoline-3-carboxamide;
4-hydroxy-N-phenethyl-cinnoline-3-carboxamide;
4-hydroxy-N-(3-methyl-phenyl)-cinnoline-3-carboxamide;
N-(4-fluoro-benzyl)-4-hydroxy-cinnoline-3-carboxamide;
4-hydroxy-N-(2-methyl-phenyl)-cinnoline-3-carboxamide;
4-hydroxy-N-(2-methoxy-phenyl)-cinnoline-3-carboxamide;
N-(2-chloro-phenyl)4-hydroxy-cinnoline-3-carboxamide;
4-hydroxy-N-(3-nitro-phenyl)-cinnoline-3-carboxamide;
N-(3-amino-phenyl)-4-hydroxy-cinnoline-3-carboxamide;
4-hydroxy-N-(3-trifluoromethyl-phenyl)-cinnoline-3-carboxamide;
N-(3-bromo-phenyl)-4-hydroxy-cinnoline-3-carboxamide;
N-(3,5-dichloro-phenyl)-4-hydroxy-cinnoline-3-carboxamide;
N-(2,3-dichloro-phenyl)-4-hydroxy-cinnoline-3-carboxamide;
N-(4-fluoro-phenyl)-4-hydroxy-cinnoline-3-carboxamide;
N-(3-fluoro-phenyl)-4-hydroxy-cinnoline-3-carboxamide;
4-hydroxy-N-(3-methoxy-phenyl)-cinnoline-3-carboxamide;
4-hydroxy-6-methyl-N-(2-pyridyl)-cinnoline-3-carboxamide;
6-chloro-4-hydroxy-N-(2-pyridyl)-cinnoline-3-carboxamide;
6-chloro-N-(4-fluoro-phenyl)-4-hydroxy-cinnoline-3-carboxamide;
6-chloro-N-(3-fluoro-phenyl)-4-hydroxy-cinnoline-3-carboxamide;
6-chloro-N-(3-chloro-phenyl)-4-hydroxy-cinnoline-3-carboxamide;
6-chloro-4-hydroxy-N-(3-methyl-phenyl)-cinnoline-3-carboxamide;
6-chloro-4-hydroxy-N-(6-methyl-2-pyridyl)-cinnoline-3-carboxamide;
6-chloro-4-hydroxy-N-phenyl-cinnoline-3-carboxamide;
4-hydroxy-6-methyl-N-phenyl-cinnoline-3-carboxamide;
4-hydroxy-6-methoxy-N-phenyl-cinnoline-3-carboxamide;
N-benzyl-6-chloro-4-hydroxy-cinnoline-3-carboxamide;
N-benzyl-4-hydroxy-6-methyl-cinnoline-3-carboxamide;
N-benzyl-4-hydroxy-6-methoxy-cinnoline-3-carboxamide;
4-hydroxy-N-(2,6-dimethyl-phenyl)-cinnoline-3-carboxamide;
6-fluoro-4-hydroxy-N-phenyl-cinnoline-3-carboxamide;
6-fluoro-4-hydroxy-N-(2-pyridyl)-cinnoline-3-carboxamide;
N-benzyl-6-fluoro-4-hydroxy-cinnoline-3-carboxamide;
6-fluoro-N-(4-fluoro-phenyl)-4-hydroxy-cinnoline-3-carboxamide;
6-fluoro-N-(3-fluoro-phenyl)-4-hydroxy-cinnoline-3-carboxamide;
6-fluoro-4-hydroxy-N-(3-methyl-phenyl)-cinnoline-3-carboxamide;
N-(3-chloro-phenyl)-6-fluoro-4-hydroxy-cinnoline-3-carboxamide;
4-hydroxy-N-(3-dimethylamino-propyl)-cinnoline-3-carboxamide;

4-hydroxy-N-(2-dimethylamino-ethyl)-cinnoline-3-carboxamide;

4-hydroxy-N-(2-morpholino-ethyl)-cinnoline-3-carboxamide;

4-hydroxy-N-[2-(1-methyl-pyrrolidin-2-yl)-ethyl]-cinnoline-3-carboxamide;

N-[(1-ethyl-pyrrolidin-2-yl)-methyl]-4-hydroxy-cinnoline-3-carboxamide;

and the pharmaceutically acceptable salts thereof, in particular the sodium and the potassium salts.

The cinnolines of formula (I) and the salts thereof, as well as the selected class thereof of formula (Ia), can be, for example, prepared by a process comprising reacting a compound of formula (II)

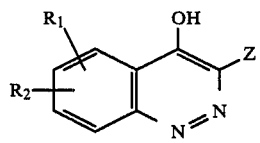

wherein
$R_1$ and $R_2$ are as defined above and Z is carboxy or a reactive functional derivative thereof, with a compound of formula (III)

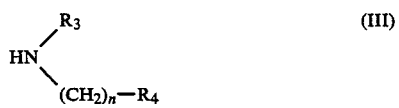

wherein n, $R_3$ and $R_4$ are as defined above; and, if desired, converting a compound of formula (I) into another compound of formula (I) and/or, if desired, converting a compound of formula (I) into a pharmaceutically acceptable salt and/or, if desired, converting a salt into a free compound and/or, if desired, separating a mixture of isomers of compounds of formula (I) into the single isomers.

When, in a compound of formula (II), Z is a reactive functional derivative of a carboxy group, it is, for example:

(a'$^v$) a $C_2$-$C_7$ alkoxycarbonyl group, preferably a $C_2$-$C_3$ alkoxycarbonyl group;

(b'$^v$) a halocarbonyl group, preferably a chlorocarbonyl or bromocarbonyl group, in particular chlorocarbonyl;

(c'$^v$) a —COOCOOR$_5$ group, wherein $R_5$ is, e.g., $C_1$-$C_6$alkyl, phenyl or benzyl.

The reaction between a compound of formula (II), wherein Z is carboxy, and a compound of formula (III) may be carried out, for example, in the presence of a condensing agent such as dicyclohexylcarbodiimide, 1,1-carbonyldiimidazole and the like, in an inert organic solvent such as benzene, dioxane, acetonitrile, at a temperature varying between about 0° C. and about 50° C.

The reaction between a compound of formula (II), wherein Z is a $C_2$-$C_7$ alkoxycarbonyl group, and a compound of formula (III), may be carried out, for example, by heating with polyphosphoric or methanesulphonic acid at a temperature varying between about 50° C. and about 200° C. in the absence of a solvent or in the presence of an inert organic solvent such as dimethylformamide, dimethylacetamide, toluene or xylene; or, alternatively, by heating from about 50° C. to about 150° C. without any acidic agent or in the presence of an aromatic hydrocarbon such as toluene or xylene, preferably distilling off slowly together with the diluent the free alkyl alcohol generated during the reaction.

The reaction between a compound fo formula (II), wherein Z is a halocarbonyl group, and a compound of formula (III) may be carried out, for example, in an inert solvent such as dichloroethane, dioxane, dimethylformamide, in the presence of pyridine or triethylamine as acid acceptor, at a temperature varying between about 0° C. and about 100° C. The reaction between a compound of formula (II) wherein Z is a —COOCOOR$_5$ group, wherein $R_5$ is defined above, and a compound of formula (II) may be carried out for example, in an inert organic solvent such as benzene, toluene, xylene, dioxane, chloroform, dichloroethane, methylene chloride or tetrahydrofuran, at a temperature varying between about 0° C. and about 50° C., preferably in the presence of a base such as triethylamine.

A compound of formula (I) may be converted, as stated above, into another compound of formula (I) by known methods; for example, a nitro group may be converted into an amino group by treatment, for example, with stannous chloride in concentrated hydrochloric acid, using, if necessary, an organic cosolvent such as acetic acid, dioxane, tetrahydrofuran, at a temperature varying between room temperature and about 100° C. Furthermore, for example, an amino group may be converted into a formylamino or a $C_2$-$C_8$ alkanoylamino group, for example by reacting with formic acid or with the suitable $C_2$-$C_8$ alkanoyl anhydride without any solvent or in an organic solvent such as dioxane, dimethylformamide, tetrahydrofuran, usually in the presence of a base such as pyridine or triethylamine, at a temperature varying between 0° C. and about 100° C.

Also the optional salification of a compound of formula (I) as well as the conversion of a salt into the free compound and the separation of a mixture of isomers into the single isomers may be carried out by conventional methods.

The compounds of formula (II), wherein Z is carboxy, may be prepared, for example, by cyclization of a compound of formula (IV)

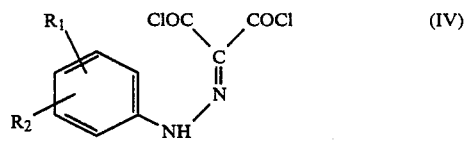

wherein $R_1$ and $R_2$ are as defined above, followed by hydrolysis of the reaction products with dilute alkali.

The cyclization of a compound of formula (IV) may be, for example, carried out by treatment with TiCl$_4$, SnCl$_4$ or AlCl$_3$, in an inert solvent such as nitrobenzene or dichloroethane at a temperature varying between the room temperature and about 100° C. The hydrolysis of the reaction products thereof may be, for example, carried out by treatment with aqueous NaOH or KOH at a temperature varying between about 0° C. and about 100° C.

The compounds of formula (II), wherein Z is halocarbonyl may be prepared, for example, by reacting the corresponding compound of formula (II), wherein Z is carboxy, with the suitable acid halide, for example oxalyl chloride, thionyl chloride, PCl$_3$, PBr$_3$, in an inert solvent such as ether, benzene, dichloroethane, dioxane, or without any solvent, at a temperature varying between about 0° C. and about 100° C.

The compounds of formula (II), wherein Z is a $C_2$–$C_7$ alkoxycarbonyl group, may be prepared, for example, by reacting the corresponding compounds of formula (II), wherein Z is halocarbonyl, with the suitable $C_1$–$C_6$ alkyl alcohol, preferably without any diluent, at a temperature varying between about 0° C. and about 100° C.

Alternatively, the compounds of formula (II), wherein Z is a $C_2$–$C_7$ alkoxycarbonyl group, may be prepared by reacting the corresponding compound of formula (II) wherein Z is carboxy with the suitable $C_1$–$C_6$ alkyl alcohol in the presence e.g. of gaseous HCl or $BF_3$.ethereate at a temperature varying between about 50° C. and about 100° C.

The compounds of formula (II), wherein Z is a group —COOCOOR$_5$, wherein R$_5$ is as defined above, may be prepared, for example, by reacting a compound of formula (II), wherein Z is a free carboxy group, with a compound of formula YCOOR$_5$, wherein R$_5$ is as defined above and Y is a halogen atom, preferably chlorine or bromine, in a solvent such as benzene, toluene, dioxane, dichloroethane, methylene chloride, chloroform, in the presence of a base such as triethylamine, at a temperature varying between about 0° C. and about 50° C.

The compounds of formula (IV) may be prepared, for example, by coupling diazotized aromatic amines of formula (V)

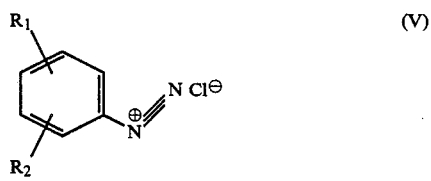

wherein R$_1$ and R$_2$ are as defined above, with diethyl malonate, e.g. in the presence of sodium acetate, to give diethyl ketomalonate phenylhydrazones of formula (VI)

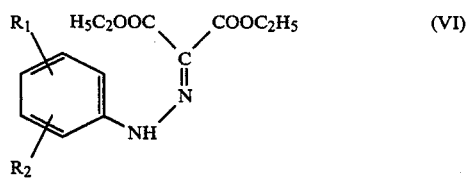

wherein R$_1$ and R$_2$ are as defined above. The compounds of formula (VI) are then hydrolyzed, for example, by treatment with aqueous NaOH or KOH in boiling ethanol, to the corresponding diacids of formula (VII)

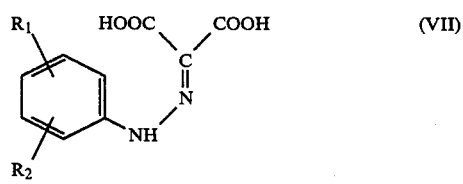

wherein R$_1$ and R$_2$ are as defined above, which in turn are reacted e.g. with $SOCl_2$ or with $PCl_5$ in an inert solvent such as benzene or dichloroethane at reflux temperature to give the compounds of formula (V).

The experimental conditions useful to obtain the compounds of formula (IV) starting from the compounds of formula (V), following the method hereabove described, have been reported by H. J. Barber in J. Chem. Soc. 2828, (1961).

The compounds of formula (III) are commercially available products or may be prepared by conventional methods. The compounds of formula (V) are known products and may be prepared by synthetic methods well known in the art. When in the compounds of the present invention and in the intermediate products thereof, groups are present, such as $NH_2$ and/or OH, which need to be protected before submitting them to the hereabove illustrated reactions, they may be protected before the reactions take place and then deprotected, according to well known methods in organic chemistry.

The compounds of formula (I) and (Ia) possess immunomodulating activity and can be used in particular as immunostimulant agents e.g. in the treatment of acute and chronic infections of both bacterial and viral origin and in the treatment of neoplastic diseases, in mammals. The immunomodulating activity of the compounds of the invention is proved, for example, by the fact that they are effective in potentiating the cytotoxic activity of the macrophages towards tumor cells in vitro.

The experimental procedure to evaluate this activity is as follows: groups of 4 mice are treated i.p. with the tested compounds and then, seven days later, peritoneal cells are collected and plated for 2 hours at 37° C. After this period the walls are washed to eliminate the non adherent cells, tumor target cells are then added and the incubation is prolonged for 48 hours. At the end of this period the target cells viability is evaluated by a colorimetric method and quantified at 570 nm.

The following table summarizes the immunostimulating activity data of some compounds of the invention, obtained according to the hereabove experimental procedure, towards TU5 tumoral cells (Eur. J. Immunol. 1982, 12, 320)

| Compound | Dose mg/kg/ip | Macrophage cytotoxic activity (% inhibition) |
|---|---|---|
| FCE 24089 | 10 | 90 |
| FCE 25008 | 50 | 71 |
| FCE 25051 | 50 | 80 |

Cytotoxic activity is calculated as % inhibition of TU5 tumoral cells growth using the following formula $$\% \text{ inhibition} = \frac{(O.D.A - O.D.B) - (O.D.C - O.D.D)}{(O.D.A - O.D.B)}$$

where

O.D.A.=optical density from cocultured TU5 and vehicol treated macrophages

O.D.B.=optical density from vehicol treated macrophages alone

O.D.C=optical density from cocultured TU5 and FCE compound treated macrophages

O.D.D=optical density from FCE compound treated macrophages alone.

FCE 24089 means 4-hydroxy-N-(2-pyridyl)-cinnoline-3-carboxamide;

FCE 25008 means 4-hydroxy-N-phenyl-cinnoline-3-carboxamide;

FCE 25051 means 4-hydroxy-N-methyl-N-(2-pyridyl)-cinnoline-3-carboxamide.

As preferred example of compounds of formula (I) or (Ia) having immunomodulating activity, the following can be mentioned:

4-hydroxy-N-(2-pyridyl)-cinnoline-3-carboxamide (internal code FCE 24089).

The compounds of the invention can be safely used in medicine.

For example, the approximate acute toxicity ($LD_{50}$) in the mouse of the compound 4-hydroxy-N-(2-pyridyl)-cinnoline-3-carboxamide determined per os with single administration of increasing doses and measured on the seventh day after the day of treatment, is higher than 800 mg/kg. Analogous toxicity data have been found for the other compounds of the invention.

The therapeutic regimen for the different clinical syndromes must be adapted to the type of pathology taking into account, as usual, also the route of administration, the form in which the compound is administered and the age, weight and conditions of the subject involved. The oral route is employed, in general, for all conditions requiring such compounds. Preference is given to intravenous injection or infusion for the treatment of acute infections.

For maintenance regimens the oral or parenteral, e.g. intramuscular or subcutaneous, route is preferred. For these purposes the compounds of the invention can be administered orally at doses ranging e.g. from about 0.5 to about 10 mg/kg of body weight per day in adult humans. Doses of active compounds ranging e.g. from about 0.2 to about 5 mg/kg of body weight can be used for the parenteral administration in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions or suspensions, tablets, pills, gelatine capsules, syrups, drops or suppositories.

Thus, for oral administration, the pharmaceutical compositions containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injection or infusion may contain as carrier, for exaple, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

It will be appreciated from the foregooing that the present invention provides the following features:

(a) The use of a compound of formula (I), or a pharmaceutically acceptable salt thereof, as immunomodulating agent.

(b) Pharmaceutical compositions having immunomodulating activity containing a compound of formula (I), or a pharmaceutically acceptable salt thereof, as active ingredient, and a suitable carrier.

(c) The use of a compound of formula (I), or a pharmaceutically acceptable salt thereof, in the preparation of a pharmaceutical composition having immunomodulating activity.

(d) 4-Hydroxy-3-cinnoline-carboxamides of formula (Ia) and the pharmaceutically acceptable salts thereof.

(e) Pharmaceutical compositions containing a suitable carrier and/or diluent and, as an active principle, a compound of formula (Ia) or a pharmaceutically acceptable salt thereof.

(f) A method of preparing cinnoline carboxamides of formula (I) and (Ia) and the pharmaceutically acceptable salts thereof.

The following examples illustrate but do not limit the invention:

EXAMPLE 1

4-Hydroxy-cinnoline-3-carboxylic acid (4 g) is reacted with $SOCl_2$ (33 g) at the reflux temperature for 2 hours. After cooling the reaction mixture is evaporated to dryness in vacuo, then the residue (4-hydroxy-cinnoline-3-carbonyl chloride) is suspended in dichloroethane (700 ml) and reacted with 3-aminopyridine (3.95 g) under stirring at room temperature for 2 hours. The precipitate is filtered and washed with dichloroethane and then with water until neutral. The product so obtained is purified over a $SiO_2$ column using chloroform-methanol-acetic acid=95:5:1 as eluent. Washing with boiling methanol yields 2.6 g of pure 4-hydroxy-N-(3-pyridyl)-cinnoline-3-carboxamide, m.p. 326°–328° C., NMR (DMSO d6) δppm: 7.3 (m) (7H; C-4, C-5 and C-6 pyridyl protons and phenyl protons), 8.87 (d) (1H, C-2 pyridyl proton), 11.95 (bs) (1H, CONH—).

By proceeding analogously the following compounds can be prepared:

4-hydroxy-N-(4-methoxy-3-pyridyl)-cinnoline-3-carboxamide;

4-hydroxy-N-phenyl-cinnoline-3-carboxamide, m.p. 335°–337° C.;
4-hydroxy-N-methyl-N-phenyl-cinnoline-3-carboxamide, m.p. 264°–266° C.;
N-ethyl-4-hydroxy-N-phenyl-cinnoline-3-carboxamide;
N-(3-chloro-phenyl)-4-hydroxy-cinnoline-3-carboxamide, m.p. 350° C. dec.;
N-(4-chloro-phenyl)-4-hydroxy-cinnoline-3-carboxamide, m.p. 362°–365° C.;
N-(3-bromo-phenyl)-4-hydroxy-cinnoline-3-carboxamide;
N-(4-fluoro-phenyl)-4-hydroxy-cinnoline-3-carboxamide;
4-hydroxy-N-(2-pyridyl)methyl-cinnoline-3-carboxamide, m.p. 280°–284° C.;
4-hydroxy-N-(3-pyridyl)methyl-cinnoline-3-carboxamide;
4-hydroxy-N-(4-methoxy-phenyl)-cinnoline-3-carboxamide, m.p. 329°–331° C.;
4-hydroxy-N-(4-methyl-phenyl)cinnoline-3-carboxamide, m.p. 335°–337° C.;
4-hydroxy-N-(3-trifluoromethyl-phenyl)-cinnoline-3-carboxamide, m.p. 332°–334° C.;
4-hydroxy-N-(4-nitro-phenyl)-cinnoline-3-carboxamide;
N-(4-chloro-phenyl)-4-hydroxy-N-methyl-cinnoline-3-carboxamide;
N-cyclohexyl-4-hydroxy-cinnoline-3-carboxamide, m.p. 249°–253° C.;
N-cyclopentyl-4-hydroxy-cinnoline-3-carboxamide;
N-benzyl-4-hydroxy-cinnoline-3-carboxamide, m.p. 284°–7° C.;
N-heptyl-4-hydroxy-cinnoline-3-carboxamide, m.p. 173°–174° C.;
N-butyl-4-hydroxy-N-methyl-cinnoline-3-carboxamide;
N-butyl-4-hydroxy-cinnoline-3-carboxamide;
N-tert.butyl-4-hydroxy-cinnoline-3-carboxamide;
N-cyclohexyl-4-hydroxy-N-methyl-cinnoline-3-carboxamide;
4-hydroxy-N,N-dioctyl-cinnoline-3-carboxamide;
N-hexadecyl-4-hydroxy-cinnoline-3-carboxamide;
4-hydroxy-N-methyl-N-octadecyl-cinnoline-3-carboxamide;
N-[(1-ethyl-pyrrolidin-2-yl)-methyl]-4-hydroxy-cinnoline-3-carboxamide;
N-(3,5-dichloro-phenyl)-4-hydroxy-cinnoline-3-carboxamide;
N-(2,3-dichloro-phenyl)-4-hydroxy-cinnoline-3-carboxamide;
N-(2-chloro-phenyl)-4-hydroxy-cinnoline-3-carboxamide;
N-(3-fluoro-phenyl)-4-hydroxy-cinnoline-3-carboxamide;
4-hydroxy-N-(3-methyl-phenyl)-cinnoline-3-carboxamide;
4-hydroxy-N-(2-methyl-phenyl)-cinnoline-3-carboxamide;
4-hydroxy-N-(2,6-dimethyl-phenyl)-cinnoline-3-carboxamide, m.p. 360°–365° C. dec.;
4-hydroxy-N-(3-methoxy-phenyl)-cinnoline-3-carboxamide;
4-hydroxy-N-(2-methoxy-phenyl)-cinnoline-3-carboxamide;
4-hydroxy-N-(3-nitro-phenyl)-cinnoline-3-carboxamide, m.p. 350° C. dec.
4-hydroxy-N-phenethyl-cinnoline-3-carboxamide;
N-(4-fluoro-benzyl)-4-hydroxy-cinnoline-3-carboxamide;
N-(2-chloro-benzyl)-4-hydroxy-cinnoline-3-carboxamide;
N-(3-methoxy-benzyl)-4-hydroxy-cinnoline-3-carboxamide;
4-hydroxy-N-(3-methoxy-benzyl)-cinnoline-3-carboxamide;
4-hydroxy-N-(2-dimethylamino-ethyl)-cinnoline-3-carboxamide;
N-(2-diethylamino-ethyl)-4-hydroxy-cinnoline-3-carboxamide;
4-hydroxy-N-[2-(4-methyl-piperazin-1-yl)-ethyl]-cinnoline-3-carboxamide;
4-hydroxy-N-(2-piperidino-ethyl)-cinnoline-3-carboxamide;
4-hydroxy-N-[2-(pyrrolidin-1-yl)-ethyl]-cinnoline-3-carboxamide;
4-hydroxy-N-[2-(1-methyl-pyrrolidin-2-yl)-ethyl]-cinnoline-3-carboxamide;
4-hydroxy-N-(2-morpholino-ethyl)-cinnoline-3-carboxamide;
4-hydroxy-N-(3-dimethylamino-propyl)-cinnoline-3-carboxamide, m.p. 196°–198° C.;
4-hydroxy-N-methyl-N-(2-dimethylamino-ethyl)-cinnoline-3-carboxamide;
N-cycloheptyl-4-hydroxy-cinnoline-3-carboxamide;
4-hydroxy-N-(3-methyl-cyclohexyl)-cinnoline-3-carboxamide; and
4-hydroxy-N-(4-methyl-cyclohexyl)-cinnoline-3-carboxamide.

EXAMPLE 2

4-Hydroxy-cinnoline-3-carboxylic acid, methyl ester (6 g), prepared accoring to J. Chem. Soc. 687 (1968), is reacted with 2-aminopyridine (16.6 g, stepwise added) in polyphosphoric acid (300 g:160 g of $H_3PO_4$ and 140 g of $P_2O_5$) under stirring at 150° C. for 10 hours. After cooling, dilution with ice water and neutralization with 35% NaOH, the precipitate is filtered and washed with water. Crystallization from dimethylformamide gives 4.9 g of 4-hydroxy-N-(2-pyridyl)-cinnoline-3-carboxamide, m.p. 341°–343° C.

By proceeding analogously the following compounds can be prepared:
4-hydroxy-N-(4-pyridyl)-cinnoline-3-carboxamide, m.p. 358°–360° C.;
4-hydroxy-N-(3-methyl-2-pyridyl)-cinnoline-3-carboxamide;
4-hydroxy-N-(4-methyl-2-pyridyl)-cinnoline-3-carboxamide;
4-hydroxy-N-(5-methyl-2-pyridyl)-cinnoline-3-carboxamide, m.p. 339°–341° C.;
4-hydroxy-N-(6-methyl-2-pyridyl)-cinnoline-3-carboxamide;
N-(5-chloro-2-pyridyl)-4-hydroxy-cinnoline-3-carboxamide, m.p. 368°–370° C.;
4-hydroxy-N-(2-thiazolyl)-cinnoline-3-carboxamide, m.p. 344°–347° C.;
4-hydroxy-N-(4-methyl-2-thiazolyl)-cinnoline-3-carboxamide; and
4-hydroxy-N-(5-methyl-3-isoxazolyl)-cinnoline-3-carboxamide.

EXAMPLE 3

4-Hydroxy-cinnoline-3-carboxylic acid (8.8 g) is dissolved in dichloromethane (600 ml) in the presence of triethylamine (5.6 g). To this solution ethyl chloroformate (6 g) diluted with dichloromethane (50 ml) is added dropwise under stirring at a temperature varying between 0° C. and about 5° C. The mixture is allowed to react at 0°–5° C. for 1 hour, then 2-methylamino-pyridine (4.55 g) is added. The reaction mixture is kept at 0°–5° C. for 1 hour, then at room temperature for 2 hours, under stirring. The organic solution is washed with 2.5% NaHCO$_3$ and water, then is evaporated to dryness in vacuo. The residue is purified over a SiO$_2$ column using ethyl acetate, then ethylacetate-methanol=95:5 as eluents. Crystallization from ethanol yields 1.65 g of 4-hydroxy-N-methyl-N-(2-pyridyl)-cinnoline-3-carboxamide, m.p. 237°–239° C., NMR (DMSO d6) δ ppm: 3.43 (s) (3H, CH$_3$), 7.0–8.3 (m) (8H, phenyl and pyridyl protons).

By proceeding analogously, the following compounds can be prepared:
6-chloro-4-hydroxy-N-methyl-N-(2-pyridyl)-cinnoline-3-carboxamide;
4-hydroxy-6,N-dimethyl-N-(2-pyridyl)-cinnoline-3-carboxamide
4-hydroxy-6-methoxy-N-methyl-N-(2-pyridyl)-cinnoline-3-carboxamide;
6-fluoro-4-hydroxy-N-methyl-N-(2-pyridyl)-cinnoline-3-carboxamide; and
8-chloro-4-hydroxy-N-methyl-N-(2-pyridyl)-cinnoline-3-carboxamide.

EXAMPLE 4

4-Hydroxy-cinnoline-3-carboxylic acid, methylester (0.6 g) is reacted with 2-amino-pyridine (0.56 g) under stirring in xylene (120 ml) at the reflux temperature for 48 hours. During the reaction 60 ml of xylene are distilled off slowly. After cooling the precipitate is filtered and washed with xylene. Crystallization from dimethylformamide yields 0.35 g of 4-hydroxy-N-(2-pyridyl)-cinnoline-3-carboxamide, m.p. 341°–343° C.

By proceeding analogously the following compounds can be prepared:
4-hydroxy-N-phenyl-cinnoline-3-carboxamide, m.p. 335°–337° C.;
4-hydroxy-N-(3-pyridyl)-cinnoline-3-carboxamide, m.p. 326°–327° C.; and
4-hydroxy-N-(4-pyridyl)-cinnoline-3-carboxamide, m.p. 358°–360° C.

EXAMPLE 5

By proceeding according to Examples 1, 2, 3 and 4 the following compounds can be prepared:
6-chloro-4-hydroxy-N-(2-pyridyl)-cinnoline-3-carboxamide, m.p. 359°–362° C.
8-chloro-4-hydroxy-N-(2-pyridyl)-cinnoline-3-carboxamide
4-hydroxy-6-methyl-N-(2-pyridyl)-cinnoline-3-carboxamide;
4-hydroxy-6-methoxy-N-(2-pyridyl)-cinnoline-3-carboxamide;
4-hydroxy-6-nitro-N-(2-pyridyl)-cinnoline-3-carboxamide;
6-chloro-4-hydroxy-N-(3-pyridyl)-cinnoline-3-carboxamide;
6-chloro-4-hydroxy-N-(4-pyridyl)-cinnoline-3-carboxamide;
6-chloro-4-hydroxy-N-phenyl-cinnoline-3-carboxamide, m.p. 350° C. dec.;
4-hydroxy-6-methoxy-N-(3-pyridyl)-cinnoline-3-carboxamide;
4-hydroxy-6-methoxy-N-(4-pyridyl)-cinnoline-3carboxamide;
4-hydroxy-6-methoxy-N-phenyl-cinnoline-3-carboxamide;
6-tert.-butyl-4-hydroxy-N-(2-pyridyl)-cinnoline-3-carboxamide;
6-fluoro-4-hydroxy-N-(2-pyridyl)-cinnoline-3-carboxamide;
6-fluoro-4hydroxy-N-phenyl-cinnoline-3-carboxamide;
4-hydroxy-6-methyl-N-phenyl-cinnoline-3-carboxamide;
6-tert.butyl-4-hydroxy-N-phenyl-cinnoline-3-carboxamide;
4-hydroxy-6-nitro-N-phenyl-cinnoline-3-carboxamide;
8-chloro-4-hydroxy-N-phenyl-cinnoline-3-carboxamide;
6,8-dichloro-4-hydroxy-N-phenyl-cinnoline-3-carboxamide;
6-chloro-4-hydroxy-N-(6-methyl-2-pyridyl)-cinnoline-3-carboxamide;
6-fluoro-4-hydroxy-N-(6-methyl-2-pyridyl)-cinnoline-3-carboxamide;
6,8-dichloro-4-hydroxy-N-(2-pyridyl)-cinnoline-3-carboxamide;
7,8-dichloro-4-hydroxy-N-(2-pyridyl)-cinnoline-3-carboxamide;
7,8-dichloro-4-hydroxy-N-phenyl-cinnoline-3-carboxamide;
4-hydroxy-6,8-dimethyl-N-phenyl-cinnoline-3-carboxamide;
4-hydroxy-6,8-dimethyl-N-(2-pyridyl)-cinnoline-3-carboxamide;
6-chloro-N-(3-chloro-phenyl)-4-hydroxy-cinnoline-3-carboxamide;
6-chloro-N-(4fluoro-phenyl)4-hydroxy-cinnoline-3-carboxamide;
6-chloro-N-(3-fluoro-phenyl)-4-hydroxy-cinnoline-3-carboxamide;
6-chloro-4-hydroxy-N-(3-methyl-phenyl)-cinnoline-3-carboxamide;
6-chloro-4-hydroxy-N-(3-methoxy-phenyl)-cinnoline-3-carboxamide;
6-chloro-4-hydroxy-N-(2,6-dimethyl-phenyl)-cinnoline-3-carboxamide;
N-benzyl-6-chloro-4-hydroxy-cinnoline-3-carboxamide;
N-benzyl-8-chloro-4-hydroxy-cinnoline-3-carboxamide;
N-benzyl-6-fluoro-4-hydroxy-cinnoline-3-carboxamide;
N-benzyl-4-hydroxy-6-methyl-cinnoline-3-carboxamide;
N-benzyl-4-hydroxy-6-methoxy-cinnoline-3-carboxamide;
N-benzyl-6,8-dichloro-4-hydroxy-cinnoline-3-carboxamide;
N-benzyl-7,8-dichloro-4-hydroxy-cinnoline-3-carboxamide;
N-benzyl-4-hydroxy-6,8-dimethyl-cinnoline-3-carboxamide;
N-benzyl-4-hydroxy-6-nitro-cinniline-3-carboxamide;
6-chloro-N-(2-chloro-phenyl)-4-hydroxy-cinniline-3-carboxamide;
6-chloro-N-(3,5-dichloro-phenyl)-4-hydroxy-cinnoline-3-carboxamide;
6-chloro-N-(2,3-dichloro-phenyl)-4-hydroxy-cinnoline-3-carboxamide;
6-chloro-4-hydroxy-N-(2-methoxy-phenyl)-cinnoline-3-carboxamide;
6-chloro-4-hydroxy-N-(2-methyl-phenyl)-cinnoline-3-carboxamide;

6-chloro-4-hydroxy-N-(3-nitro-phenyl)-cinnoline-3-carboxamide;
6-fluoro-N-(3-fluoro-phenyl)-4-hydroxy-cinnoline-3-carboxamide;
6-fluoro-N-(4-fluoro-phenyl)-4-hydroxy-cinnoline-3-carboxamide;
N-(3-chloro-phenyl)-6-fluoro-4-hydroxy-cinnoline-3-carboxamide;
N-(3-chloro-phenyl)-4-hydroxy-6-methoxy-cinnoline-3-carboxamide;
N-(3-fluoro-phenyl)-4-hydroxy-6-methoxy-cinnoline-3-carboxamide;
N-(4-fluoro-phenyl)-4-hydroxy-6-methoxy-cinnoline-3-carboxamide;
N-(3-chloro-phenyl)-4-hydroxy-6-methyl-cinnoline-3-carboxamide;
6-fluoro-4-hydroxy-N-(3-methyl-phenyl)-cinnoline-3-carboxamide;
N-(3-fluoro-phenyl)-4-hydroxy-6-methyl-cinnoline-3-carboxamide;
N-(4-fluoro-phenyl)-4-hydroxy-6-methyl-cinnoline-3-carboxamide;
8-chloro-N-(3-chloro-phenyl)-4-hydroxy-cinniline-3-carboxamide;
8-chloro-N-(4-fluoro-phenyl)-4-hydroxy-cinnoline-3-carboxamide;
8-chloro-N-(3-fluoro-phenyl)-4-hydroxy-cinnoline-3-carboxamide;
8-chloro-4-hydroxy-N-(3-methyl-phenyl)-cinnoline-3-carboxamide;
6-tert.butyl-N-(4-fluoro-phenyl)-4-hydroxy-cinnoline-3-carboxamide;
6-tert.butyl-N-(3-fluoro-phenyl)-4-hydroxy-cinnoline-3-carboxamide; and
6-tert.butyl-N-(3-chloro-phenyl)-4-hydroxy-cinnoline-3-carboxamide.

EXAMPLE 6

4-Hydroxy-N-(3-nitro-phenyl)-cinnoline-3-carboxamide (3.1 g) is reacted with SnCl$_2$.2H$_2$O (22.5 g) in 37% HCl (16 ml) and acetic acid (144 ml) under stirring at 90° C. for 3 hours.

After cooling the precipitate is filtered and washed with acetic acid, then suspended in 2N NaOH under stirring for 1 hour. The product is filtered and washed with water, then treated with hot 5% aqueous NaH$_2$PO$_4$ under stirring, filtered and washed with water until neutral. Crystallization from dimethylformamide/ethanol gives 2.3 g of N-(3-amino-phenyl)-4-hydroxy-cinnoline-3-carboxamide.

By proceeding analogously the following compounds can be prepared:
6-amino-4-hydroxy-N-(2-pyridyl)-cinnoline-3-carboxamide;
6-amino-4-hydroxy-N-phenyl-cinnoline-3-carboxamide;
6-amino-N-benzyl-4-hydroxy-cinnoline-3-carboxamide; and
N-(4-amino-phenyl)-4-hydroxy-cinnoline-3-carboxamide.

EXAMPLE 7

N-(3-Amino-phenyl)-4-hydroxy-cinnoline-3-carboxamide (1 g) is reacted with acetic anhydride (5 ml) in dimethylformamide (50 ml) in the presence of pyridine (5 ml) at 80° C. for 2 hours. After cooling the reaction mixture is diluted with ice water and the precipitate is filtered and washed with water: washing with hot ethanol gives 0.75 g of N-(3-acetylamino-phenyl)-4-hydroxy-cinnoline-3-carboxamide.

By proceeding analogously the following compounds can be prepared:
6-acetylamino-4-hydroxy-N-(2-pyridyl)-cinnoline-3-carboxamide;
6-acetylamino-4-hydroxy-N-phenyl-cinnoline-3-carboxamide;
N-(4-acetylamino-phenyl)-4-hydroxy-cinnoline-3-carboxamide; and
6-acetylamino-N-benzyl-4-hydroxy-cinnoline-3-carboxamide.

EXAMPLE 8

4-Hydroxy-N-(3-pyridyl)-cinnoline-3-carboxamide is dissolved by treatment with an equivalent amount of sodium ethoxide in ethanol. The solutions is evaporated to dryness and the residue is treated with isopropyl ether and then filtered to give the sodium salt of 4-hydroxy-N-(3-pyridyl)-cinnoline-3-carboxamide, m.p. >300° C.

By proceeding analogously the following compounds can be prepared:
4-hydroxy-N-(2-pyridyl)-cinnoline-3-carboxamide, sodium salt;
4-hydroxy-4-phenyl-cinnoline-3-carboxamide, sodium salt; and
N-benzyl-4-hydroxy-cinnoline-3-carboxamide, sodium salt.

EXAMPLE 9

Tablets, each weighing 150 mg and containing 50 mg of active substance, can be manufactured as follows:

Composition (for 10,000 tablets)

| | |
|---|---|
| 4-hydroxy-N—(2-pyridyl)-cinnoline-3-carboxamide | 500 g |
| Lactose | 710 g |
| Corn starch | 238 g |
| Talc powder | 36 g |
| Magnesium stearate | 16 g |

4-hydroxy-N-(2-pyridyl)-cinnoline-3-carboxamide, lactose and half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm; then the remaining quantity of starch, talc and magnesium stearate is added, carefully mixed and processed into tablets using punches of 8 mm diameter.

By proceeding analogously tablets can be prepared having the same composition, but containing, for example, as active substance one of the following compounds:
4-hydroxy-N-(6-methyl-2-pyridyl)-cinnoline-3-carboxamide;
4-hydroxy-N-phenyl-cinnoline-3-carboxamide;
6-chloro-4-hydroxy-N-phenyl-cinnoline-3-carboxamide; and
4-hydroxy-N-methyl-N-(2-pyridyl)-cinnoline-3-carboxamide.

We claim:
1. A method of treating bacterial or viral infection in a mammal in need of such treatment, which comprises administering to the mammal an effective amount of a compound of formula (I)

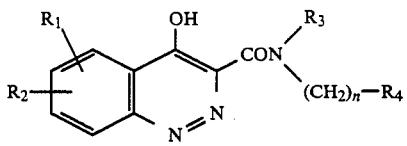 (I)

wherein
n is zero, 1 or 2;
each of $R_1$ and $R_2$ is independently:
(a) hydrogen, halogen, trifluoromethyl or $C_1$-$C_6$ alkyl;
(b) hydroxy, $C_1$-$C_6$ alkoxy or $C_3$-$C_4$ alkenyloxy;
(c) nitro, amino, formylamino or $C_2$-$C_8$ alkanoylamino;
$R_3$ represents hydrogen or $C_1$-$C_8$ alkyl;
$R_4$ is:
(a') $C_1$-$C_{20}$ alkyl, unsubstituted or substituted by

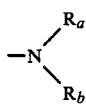

wherein each of $R_a$ and $R_b$ is independently phenyl or $C_1$-$C_6$ alkyl, or $R_a$ and $R_b$, taken together with the nitrogen atom to which they are linked, form a N-pyrrolidinyl, N-piperazinyl, hexahydroazepin-1-yl, thiomorpholino, morpholino or piperidino ring, wherein said heterocyclic rings may be unsubstituted or substituted by $C_1$-$C_6$ alkyl or phenyl;
(b') $C_5$-$C_{10}$ cycloalkyl, unsubstituted or substituted by methyl;
(c') 2- or 3-pyrrolidinyl, piperidyl or 2-piperazinyl, wherein said heterocyclic rings may be unsubstituted or substituted by $C_1$-$C_6$ alkyl;
(d') isoxazolyl or thiazolyl, wherein said heterocyclic rings may be unsubstituted or substituted by $C_1$-$C_6$ alkyl;
(e') pyridyl, unsubstituted or substituted by one or two substituents chosen independently from halogen, $C_1$-$C_6$ alkyl and $C_1$-$C_6$ alkoxy; or
(f') phenyl, unsubstituted or substituted by one or two substituents chosen independently from halogen, $CF_3$, $C_1$-$C_6$ alkyl, $C_1$-$C_6$ alkoxy, 1 amino, nitro, formylamino and $C_2$-$C_8$ alkanoylamino; or a pharmaceutically acceptable salt thereof.

2. A method according to claim 1, wherein, in the compound of formula (I), n is zero, $R_1$ and $R_2$ are hydrogen, $R_3$ is hydrogen or $C_1$-$C_4$ alkyl, and $R_4$ is phenyl or pyridyl, unsubstituted or substituted by one or more methyl groups.

3. A method according to claim 1, wherein the compound of formula (I) is 4-hydroxy-N-(4-pyridyl)-cinnoline-3-carboxamide; 4-hydroxy-N-(2-pyridyl-cinnoline-3-carboxamide); 4-hydroxy-N-phenyl-cinnoline-3-carboxamide; 4-hydroxy-N-methyl-N-(2-pyridyl)-cinnoline-3-carboxamide and 4-hydroxy-N-(2,6-dimethylphenyl)-cinnoline-3-carboxamide; or a pharmaceutically acceptable salt thereof.

4. A method of stimulating the immunity system in a mammal in need of such stimulation, which comprises administering to the mammal an immunostimulant effective amount of a compound of formula (I)

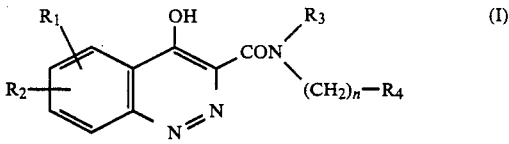 (I)

wherein
n is zero, 1 or 2;
each of $R_1$ and $R_2$ is independently:
(a) hydrogen, halogen, trifluoromethyl or $C_1$-$C_6$ alkyl;
(b) hydroxy, $C_1$-$C_6$ alkoxy or $C_3$-$C_4$ alkenyloxy;
(c) nitro, amino, formylamino or $C_2$-$C_8$ alkanoylamino;
$R_3$ represents hydrogen or $C_1$-$C_8$ alkyl;
$R_4$ is:
(a') $C_1$-$C_{20}$ alkyl, unsubstituted or substituted by

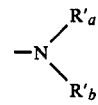

wherein each of $R_a$ and $R_b$ is independently phenyl or $C_1$-$C_6$ alkyl, or $R_a$ and $R_b$, taken together with the nitrogen atom to which they are linked, form a N-pyrrolidinyl, N-piperazinyl, hexahydroazepin-1-yl, thiomorpholino, morpholino or piperidino ring, wherein said heterocyclic rings may be unsubstituted or substituted by $C_1$-$C_6$ alkyl or phenyl;
(b') $C_5$-$C_{10}$ cycloalkyl, unsubstituted or substituted by methyl;
(c') 2- or 3-pyrrolidinyl, piperidyl or 2-piperazinyl, wherein said heterocyclic rings may be unsubstituted or substituted by $C_1$-$C_6$ alkyl;
(d') isoxazolyl or thiazolyl, wherein said heterocyclic rings may be unsubstituted or substituted by $C_1$-$C_6$ alkyl;
(e') pyridyl, unsubstituted or substituted by one or two substitutents chosen independently from halogen, $C_1$-$C_6$ alkyl and $C_1$-$C_6$ alkoxy; or
(f') phenyl, unsubstituted or substituted by one or two substituents chosen independently from halogen, $CF_3$, $C_1$-$C_6$ alkyl, $C_1$-$C_6$ alkoxy, amino, nitro, formylamino and $C_2$-$C_8$ alkanoylamino; or a pharmaceutically acceptable salt thereof.

5. A method according to claim 4 wherein, in the compound of formula (I), n is zero, $R_1$ and $R^2$ are hydrogen, $R_3$ is hydrogen or $C_{1-4}$ alkyl, and $R_4$ is phenyl or pyridyl, unsubstituted or substituted by one or two methyl groups.

6. A method according to claim 4, wherein the compound of formula (I) is 4-hydroxy-N-(4-pyridyl)-cinnoline-3-carboxamide; 4-hydroxy-N-2-pyridyl-cinnoline-3-carboxamid): 4-hydroxy-N-phenyl-cinnoline-3-carboxamide; and 4-hydroxy-N-methyl-N-(2-pyridyl)-cinnoline-3-carboxamide; or a pharmaceutically acceptable salt thereof.

7. A method according to claim 1, wherein the compound of formula (I) is 4-hydroxy-N-(5-methyl-2-pyridyl)-cinnoline-3-carboxamide, or a pharmaceutically acceptable salt thereof.

8. A method according to claim 4, wherein the compound of formula (I) is 4-hydroxy-N-(5-methyl-2-pyridyl)-cinnoline-3-carboxamide, or a pharmaceutically acceptable salt thereof.

* * * * *